United States Patent
Kim et al.

(10) Patent No.: US 9,161,739 B2
(45) Date of Patent: Oct. 20, 2015

(54) BEAMFORMING METHOD, BEAMFORMING APPARATUS, AND MEDICAL IMAGING SYSTEM PERFORMING THE BEAMFORMING METHOD

(71) Applicants: SAMSUNG ELECTRONICS CO., LTD., Suwon-si (KR); INDUSTRY ACADEMIC COOPERATION FOUNDATION, HALLYM UNIVERSITY, Chuncheon-si (KR)

(72) Inventors: Kyu-hong Kim, Seongnam-si (KR); Sung-Chan Park, Suwon-si (KR); Jung-ho Kim, Yongin-si (KR); Moo-ho Bae, Chuncheon-si (KR)

(73) Assignees: SAMSUNG ELECTRONICS CO., LTD., Suwon-si (KR); Industry Academic Cooperation Foundation, Hallym University, Chuncheon-si (KR)

( * ) Notice: Subject to any disclaimer, the term of this patent is extended or adjusted under 35 U.S.C. 154(b) by 0 days.

(21) Appl. No.: 13/680,741

(22) Filed: Nov. 19, 2012

(65) Prior Publication Data
US 2013/0131514 A1    May 23, 2013

(30) Foreign Application Priority Data
Nov. 17, 2011  (KR) .................. 10-2011-0120315

(51) Int. Cl.
A61B 8/14 (2006.01)
A61B 8/08 (2006.01)
G01S 15/89 (2006.01)
G01S 7/52 (2006.01)

(52) U.S. Cl.
CPC ................ *A61B 8/14* (2013.01); *A61B 8/5207* (2013.01); *G01S 7/52047* (2013.01); *G01S 15/8977* (2013.01)

(58) Field of Classification Search
CPC ............ G01S 15/8961; G01S 15/8963; G01S 15/8977; G01S 7/52028; G01S 7/52038; G01S 7/52047; A61B 8/14; A61B 8/5207
USPC ................................................. 600/437–469
See application file for complete search history.

(56) References Cited

U.S. PATENT DOCUMENTS

| | | | |
|---|---|---|---|
| 6,436,044 B1 | 8/2002 | Wang | |
| 6,527,720 B1 | 3/2003 | Ustuner et al. | |
| 6,909,796 B2* | 6/2005 | Pomata et al. | 382/131 |
| 7,099,630 B2* | 8/2006 | Brunner et al. | 455/69 |

(Continued)

FOREIGN PATENT DOCUMENTS

| | | |
|---|---|---|
| KR | 10-2006-0086821 A | 8/2006 |
| KR | 10-0886932 B1 | 3/2009 |

OTHER PUBLICATIONS

Communication dated Mar. 6, 2013 from the European Patent Office in counterpart European application No. 12190824.8.

(Continued)

*Primary Examiner* — Sanjay Cattungal
(74) *Attorney, Agent, or Firm* — Sughrue Mion, PLLC (57) ABSTRACT

A beamforming apparatus includes a storage for storing a plurality of basis vectors obtained from a beamforming coefficient of a previously-measured echo signal; a weight calculator for calculating a weight to be applied to an echo signal reflected from a target; and a synthesizer for applying the weight to the echo signal reflected from the target and synthesizing signals to which the weight is applied.

20 Claims, 5 Drawing Sheets

(56) References Cited

U.S. PATENT DOCUMENTS

2002/0028009 A1* 3/2002 Pomata et al. .............. 382/131
2009/0198138 A1 8/2009 Uchikawa et al.
2012/0035477 A1* 2/2012 Tashiro ..................... 600/443

OTHER PUBLICATIONS

Asl et al., "Eigenspace-Based Minimum Variance Beamforming Applied to Medical Ultrasound Imaging", IEEE Transactions on Ultrasonics, Ferroelectrics and Frequency Control, vol. 57, No. 11, Nov. 1, 2010, pp. 2381-2390.

Synnevåg, Johan-Fredrik, et al., "A Low Complexity Data-Dependent Beamformer," IEEE International Ultrasonics Symposium Proceedings, 2008, pp. 1084-1087.

Capon, J., "High-Resolution Frequency-Wavenumber Spectrum Analysis," Proceedings of the IEEE, vol. 57, No. 8, Aug. 1969, pp. 1408-1418.

* cited by examiner

BEAMFORMING METHOD, BEAMFORMING APPARATUS, AND MEDICAL IMAGING SYSTEM PERFORMING THE BEAMFORMING METHOD

CROSS-REFERENCE TO RELATED APPLICATION

This application claims priority from Korean Patent Application No. 10-2011-0120315, filed on Nov. 17, 2011, in the Korean Intellectual Property Office, the disclosure of which is incorporated herein in its entirety by reference.

BACKGROUND

1. Field

Apparatuses and methods consistent with exemplary embodiments relate to a beamforming method, a beamforming apparatus, and a medical imaging system performing the beamforming method.

2. Description of the Related Art

A medical imaging system may use a fixed beamforming technique or an adaptive beamforming technique. The fixed beamforming technique uses a Hamming window or a Hanning window, regardless of an input signal, and corresponds to data-independent beamforming. The adaptive beamforming technique uses a beamforming coefficient according to an input signal, and corresponds to data-dependent beamforming.

SUMMARY

According to one or more of exemplary embodiments, a beamforming method, a beamforming apparatus, and a medical imaging system performing the beamforming method to generate a high-definition diagnostic image.

According to one or more of exemplary embodiments, a non-transitory computer-readable recording medium has recorded thereon a program for executing the beamforming method, by using a computer.

According to an aspect of an exemplary embodiment, a beamforming apparatus includes a storage which stores a plurality of basis vectors obtained from beamforming coefficients of previously-measured echo signals; a weight calculator which calculates weights to be applied to echo signals reflected from a target, by using the plurality of basis vectors; and a synthesizer which applies the weights to the echo signals reflected from the target, and synthesizes the echo signals to which the weights are applied.

According to another aspect of an exemplary embodiment, a medical imaging system includes a beamforming apparatus which calculates weights to be applied to echo signals reflected from a target, by using a plurality of basis vectors obtained from beamforming coefficients of previously-measured echo signals, applies the weights to the echo signals reflected from the target object, and synthesizes the echo signals to which the weights are applied; and a diagnostic image generator which generates a diagnostic image by using signals output from the beamforming apparatus.

According to another aspect of an exemplary embodiment, a beamforming method includes operations of calculating weights to be applied to echo signals reflected from a target, by using a plurality of basis vectors obtained from beamforming coefficients of previously-measured echo signals; and applying the weights to the echo signals reflected from the target, and synthesizing the echo signals to which the weights are applied.

According to another aspect of an exemplary embodiment, a method includes perations of obtaining basis vectors from beamforming coefficients of previously-measured echo signals; storing, in a storage, a number r of the obtained basis vectors, the number r being greater than or equal to 1; projecting echo signals reflected from a target on the basis vectors; calculating weights based on the echo signals projected on the basis vectors; applying the weights to the projected echo signals; and synthesizing the weighted echo signals.

According to another aspect of an exemplary embodiment, there is provided a computer-readable recording medium having recorded thereon a program for executing the beamforming method, by using a computer.

BRIEF DESCRIPTION OF THE DRAWINGS

The above and/or other aspects will become apparent by describing certain exemplary embodiments, with reference to the accompanying drawings, in which.

DETAILED DESCRIPTION

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be carried out without those specifically defined matters. Also, well-known functions or constructions are not described in detail since that would obscure the invention with unnecessary detail.

Figure 1:
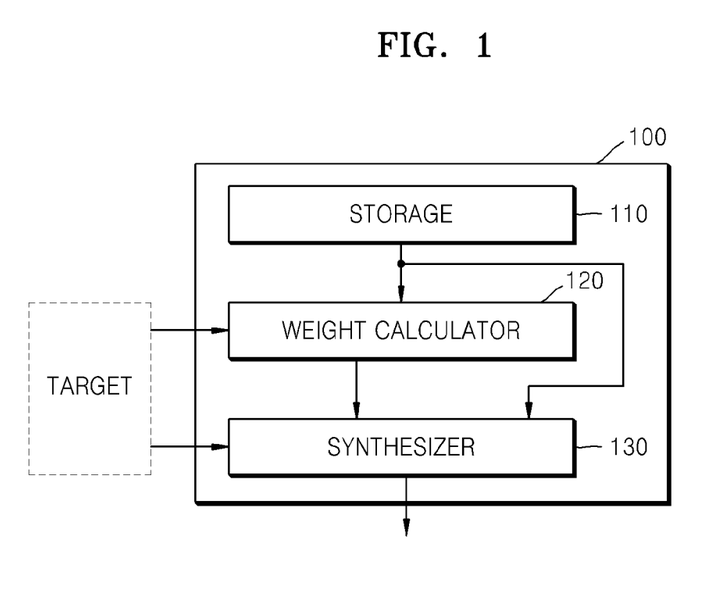
FIG. 1 is a diagram of a beamforming apparatus according to an exemplary embodiment.

FIG. 1 is a diagram of a beamforming apparatus 100 according to an exemplary embodiment. Referring to FIG. 1, the beamforming apparatus 100 includes a storage 110, a weight calculator 120, and a synthesizer 130.

FIG. 1 illustrates the elements of the beamforming apparatus 100 which are related to describing the present exemplary embodiment. However, the beamforming apparatus 100 may further include other elements in addition to the elements shown in FIG. 1.

For example, the weight calculator 120 and the synthesizer 130 in the beamforming apparatus 100 of FIG. 1 may be implemented by one or more processors. The processor may be embodied as an array of a plurality of logic gates, or as a combination of a general-use microprocessor and memory storing programs to be executed by the general-use microprocessor. However, the processor may be embodied based on other appropriate hardware.

The beamforming apparatus 100 forms a reception beam by using an echo signal reflected from a target or an object. For example, the target may include the abdomen, the heart, and the like of a human body, and the echo signal may be an ultrasonic signal reflected from the target, but are not limited thereto.

The storage 110 stores a plurality of basis vectors obtained from a beamforming coefficient of a previously-measured echo signal. The beamforming coefficient may be a weight to be applied to each channel or each sub-array. The channel may be a transducer that receives an echo signal, and the sub-array may indicate a sub-aperture that includes a plurality of the transducers, but are not limited thereto.

The previously-measured echo signal may be an echo signal reflected from a predetermined target, which may be the same as the target with respect to the echo signal to which beamforming is currently performed by the beamforming apparatus 100, but is not limited thereto.

For example, the storage 110 may store the basis vectors that are obtained by performing a principal component analysis (PCA) on the beamforming coefficient of the previously-measured echo signal.

In more detail, the beamforming coefficient of the previously-measured echo signal may be calculated for each channel or each sub-array according to a minimum variance technique. For example, the beamforming coefficient that is calculated according to the minimum variance technique may be an optimal weight.

By performing the PCA by using a variance of the beamforming coefficient calculated according to the minimum variance technique, a plurality of eigenvectors may be obtained, and some of the obtained eigenvectors may be stored in the storage 110, as the basis vectors.

For example, the basis vectors stored in the storage 110 may correspond to the predetermined number of vectors according to an order of larger eigenvalues from among the eigenvectors obtained by performing the PCA. A user may determine the number of basis vectors to be stored in the storage 110, and the determined number of basis vectors may be stored in the storage 110. The user of the beamforming apparatus 100 may be a medical staff including doctors, nurses, medical image technicians, and the like, but are not limited thereto and, thus, may include a designer of the beamforming apparatus 100, or the like.

The eigenvectors and the basis vectors that are obtained by performing the PCA will be described in detail with reference to FIGS. 2A and 2B.

The storage 110 is a general storage medium including a hard disk drive (HDD), a read-only memory (ROM), a random access memory (RAM), a flash memory, and/or a memory card.

The weight calculator 120 calculates a weight to be applied to the echo signal reflected from the target, by using the basis vectors stored in the storage 110. The weight calculated by the weight calculator 120 may be used as a parameter that forms an apodization function. For example, the echo signal reflected from the target may be radio frequency (RF) data.

The weight calculator 120 may calculate the weight by using all of the basis vectors stored in the storage 110, or alternatively, the weight calculator 120 may calculate the weight by using a predetermined number of basis vectors according to a user's determination.

For example, the echo signal that is used by the weight calculator 120 to calculate the weight may be an echo signal to which a time delay value for beamforming is applied, but is not limited thereto. The time delay value for beamforming may be a time delay value for compensating for an error due to a distance between a focal point and the transducer.

An example below corresponds to a case in which the echo signal reflected from the target is received by M channels, but is not limited thereto and, thus, the echo signal reflected from the target may be received by M sub-arrays.

The weight calculator 120 may calculate the weight to be applied to the echo signal reflected from the target, by using a predetermined number, less than M, of the basis vectors from among the basis vectors stored in the storage 110.

In more detail, the weight calculator 120 may project the echo signal reflected from the target to each of the basis vectors stored in the storage 110, and may calculate the weight by using the projected echo signal. This will be described in detail with reference to the weight calculator 120 of FIG. 3.

As described above, since the weight calculator 120 calculates the weight by using the echo signal projected to the basis vectors, a dimension of the echo signal is decreased, so that the computational amount with respect to the calculation of the weight may be substantially decreased.

The synthesizer 130 applies the weight, which is calculated by the weight calculator 120, to the echo signal reflected from the target, by using the basis vectors stored in the storage 110, and synthesizes signals to which the weight is applied. For example, the synthesizer 130 may apply the weight to the echo signal to which the time delay value for beamforming is applied and which is projected to the basis vectors.

The synthesizer 130 may apply the weight to the echo signal by using all of the basis vectors stored in the storage 110, or alternatively, the synthesizer 130 may apply the weight to the echo signal by using a predetermined number of basis vectors according to a user's determination.

For example, the synthesizer 130 may apply a weighted sum with respect to all or some of the basis vectors to the echo signal reflected from the target. In this case, weights for applying the weighted sum with respect to the basis vectors may correspond to the weights calculated by the weight calculator 120.

For example, the synthesizer 130 synthesizes the signals to which the weight is applied. The synthesizer 130 may output the reception beam formed according to a result of the synthesis of the signals to which the weight is applied.

For example, the synthesizer 130 may sum the signals to which the weight is applied, thereby forming one reception beam. By summing the signals to which the weight is applied, the synthesizer 130 may estimate an ultrasonic signal reflected from the focal point.

Accordingly, the beamforming apparatus 100 may form the reception beam for generating a high-resolution diagnostic image while the computational amount is substantially decreased.

Figure 2A:
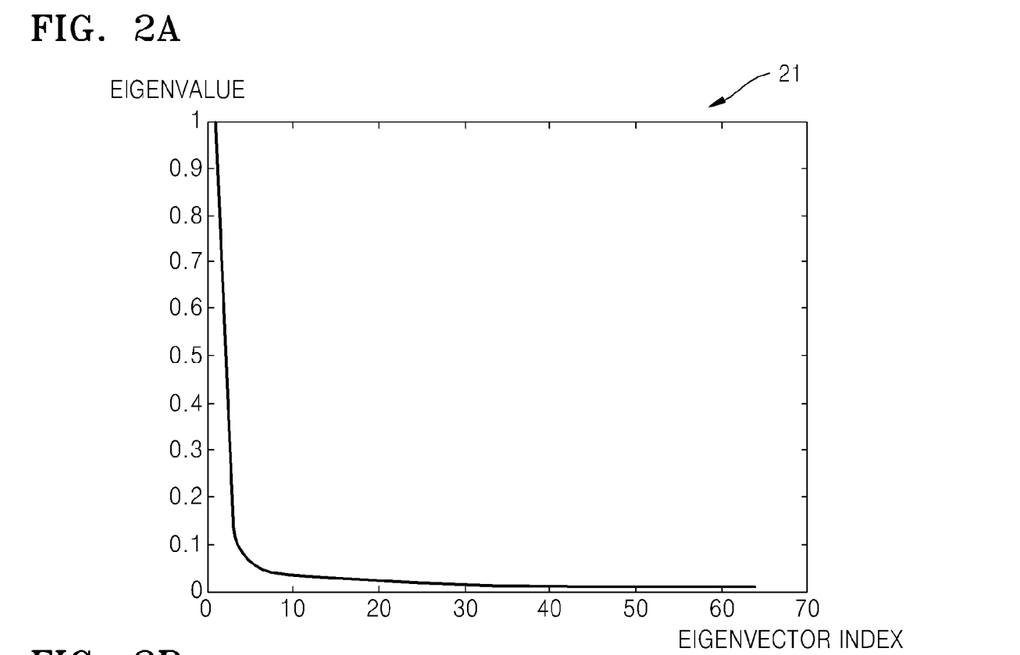
FIGS. 2A and 2B illustrate examples of eigenvectors and basis vectors, according to an exemplary embodiment.
Figure 2B:
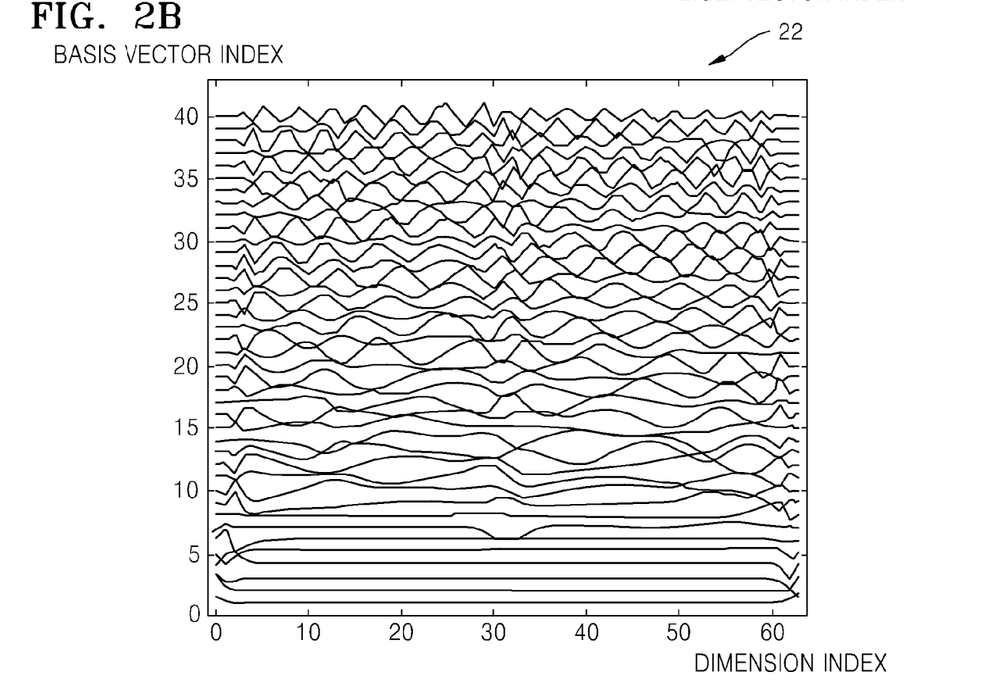

FIGS. 2A and 2B illustrate examples of eigenvectors and basis vectors, according to an exemplary embodiment. In FIG. 2A, a graph 21 indicating the eigenvectors is illustrated. In FIG. 2B, a graph 22 indicating the basis vectors is illustrated.

For convenience of description, in FIGS. 2A and 2B, it is assumed that a PCA is performed by using beamforming coefficients with respect to 64 channels calculated according to a minimum variance technique, and 40 basis vectors are stored in the storage 110. However, an exemplary embodiment is not limited thereto.

The graph 21 indicating the eigenvectors shows a result obtained by performing the PCA on the beamforming coefficients with respect to 64 channels. Referring to the graph 21, the eigenvectors that are generated according to a result of the PCA are arranged in order, according to a decreasing magnitude of eigenvalues. For example, a first eigenvector, whose eigenvector index is 1, has a maximum eigenvalue. As an index of each eigenvector is increased, a corresponding eigenvalue is decreased.

The graph 22 indicates 40 basis vectors. The graph 22 shows first through 40th eigenvectors whose eigenvector indexes are equal to or less than 40 and which are selected from among the eigenvectors. For example, the first through 40th eigenvectors of the graph 22 may correspond to the basis vectors stored in the storage 110. For example, the basis vectors may have a predetermined dimension, and, thus, the graph 22 shows the basis vectors according to dimension indexes.

The storage 110 may store 40 basis vectors, and the weight calculator 120 and the synthesizer 130 may calculate and apply the weight by using 40 or fewer basis vectors according to a user's determination.

Figure 3:
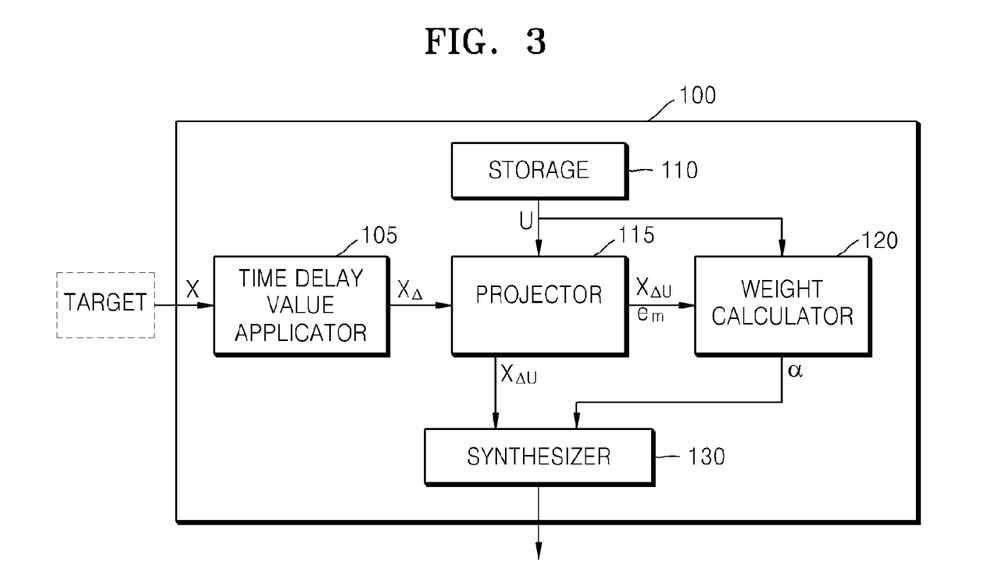
FIG. 3 is a diagram illustrating the beamforming apparatus according to an exemplary embodiment.

FIG. 3 is a diagram illustrating the beamforming apparatus 100 according to an exemplary embodiment. Referring to FIG. 3, the beamforming apparatus 100 includes a time delay value applicator 105, the storage 110, a projector 115, the weight calculator 120, and the synthesizer 130.

FIG. 3 illustrates the elements of the beamforming apparatus 100 which are related to describing the present exemplary embodiment. However, the beamforming apparatus 100 may further include other elements in addition to the elements shown in FIG. 3.

For example, the time delay value applicator 105, the projector 115, the weight calculator 120 and the synthesizer 130 in the beamforming apparatus 100 of FIG. 3 may be implemented by one or more processors.

The beamforming apparatus 100 of FIG. 3 corresponds to an exemplary beamforming apparatus 100 of FIG. 1 and is not limited to the elements shown in FIG. 3. Also, an exemplary embodiment described above with reference to FIG. 1 is applicable to the beamforming apparatus 100 of FIG. 3, and, thus, the redundant description is omitted.

The beamforming apparatus 100 forms a reception beam by using an echo signal reflected from a target object. For example, the beamforming apparatus 100 may perform calculation as Equation 1 below.

$$z[n] = \sum_{m=0}^{M-1} w_m[n] \cdot x_m[n - \Delta_m[n]]$$ [Equation 1]

In Equation 1, z[n] may indicate a result of beamforming;
n may indicate a position in the depth direction;
M may indicate the number of reception channels or reception sub-arrays;
$w_m[n]$ may indicate a beamforming coefficient;
$x_m[n]$ may indicate an echo signal;
$\Delta_m[n]$ may indicate a time delay value; and
$x_m[n-\Delta_m[n]]$ may indicate a delayed echo signal.

For example, z[n] may indicate a result of beamforming at a position n of the target in a depth direction. The position n in the depth direction may be a focal point, and z[n] according to the result of beamforming may indicate the reception beam formed according to the result of the beamforming.

A value M may indicate the number of reception channels involving the beamforming or the number of reception sub-arrays involving the beamforming. Hereinafter, it is assumed that M indicates the number of reception channels, and m indicates an $m^{th}$ reception channel from among the M reception channels. However, M may indicate the number of reception sub-arrays, and m may indicate an $m^{th}$ reception sub-array from among the M reception sub-arrays.

A value $w_m[n]$ may indicate a beamforming coefficient to be applied to an $m^{th}$ channel at the position n. For example, the beamforming coefficient may be an apodization window or a weight, and the $m^{th}$ channel may be an $m^{th}$ transducer.

A value $x_m[n]$ may indicate an echo signal that is reflected at the position n and is received by the $m^{th}$ channel, and $\Delta_m[n]$ may indicate a time delay value that is compensated according to a distance between the position n and a position of the $m^{th}$ channel, when a transmission signal or a reception signal is transmitted between the position n and the $m^{th}$ channel.

Thus, a delayed echo signal $x_m[n-\Delta_m[n]]$ may be an echo signal that is reflected at the position n, is received by the $m^{th}$ channel, and has the time delay value applied thereto.

The beamforming apparatus 100 may form one RF scanline by using echo signals with respect to a plurality of pieces of channel data. The beamforming apparatus 100 may apply the time delay value according to each channel to the echo signal reflected from the target, in consideration of the position n in the depth direction, may apply the weight to the echo signal to which the time delay value is applied, may synthesize echo signals to which the weight is applied, and according to a result of the synthesis, the beamforming apparatus 100 may estimate a reception beam indicating an ultrasonic signal reflected from the position n.

Equation 1 in a vector form is defined as Equation 2 below.

$$Z[n] = W^H[n] \cdot X_\Delta[n] = X_\Delta^T[n] \cdot W[n]$$ [Equation 2]

In Equation 2, Z[n] may indicate a beamforming result,
W[n] may indicate a weight,
$X_\Delta[n]$ may indicate an echo signal to which a time delay value is applied,
an upper suffix H may indicate a Hermitian transpose, and
an upper suffix T may indicate a transpose.

As described above, the beamforming apparatus 100 may form the reception beam by applying the time delay value and the weight to the echo signals reflected from the target. For example, the beamforming apparatus 100 decreases a dimension of a weight vector space, while the beamforming apparatus 100 does not substantially affect resolution, and substantially decreases the computational amount. That is, the beamforming apparatus 100 calculates the weight by using a plurality of basis vectors, so that the beamforming apparatus 100 may decrease the dimension of the weight vector space. For example, a level of the resolution may correspond to a level obtained according to a minimum variance technique.

The time delay value applicator 105 applies the time delay values to the corresponding echo signals reflected from the target. The corresponding time delay value according to the present exemplary embodiment may be a time delay value for compensating for an error due to a distance between a focal point and a corresponding transducer.

This will now be described with reference to Equation 1. The time delay value applicator 105 may output the delayed echo signal $x_m[n-\Delta_m[n]]$ by applying the time delay value $\Delta_m[n]$ to the echo signal $x_m[n]$ reflected from the target object. In this manner, the echo signal to which the time delay value is applied by the time delay value applicator 105 may be $X_\Delta[n]$ of Equation 2.

The storage 110 stores the basis vectors obtained from a beamforming coefficient of a previously-measured echo signal. For example, the basis vectors stored in the storage 110 may indicate a group of the basis vectors.

The projector 115 projects the echo signal, which is reflected from the target object, on each of at least some of the basis vectors stored in the storage 110. For example, the echo signal reflected from the target may be the echo signal $X_\Delta$ to which the time delay value is applied output from the time delay value applicator 105.

The number of the at least some of the basis vectors which are projection targets by the projector 115 may be determined by a user. In a case where 40 basis vectors are stored in the storage 110, the projector 115 projects the echo signal to which the time delay value is applied on each of 40 or fewer basis vectors according to a user's determination.

The projector 115 projects the echo signal on the basis vectors by the number of basis vectors according to the user's determination, so that a dimension of the echo signal may be decreased.

In more detail with respect to the projection performed by the projector 115, the beamforming result of Equation 2 may be defined as Equation 3 below.

$$Z = X_A^T W = X_A^T U^T \alpha \qquad \text{[Equation 3]}$$

In Equation 3, Z may indicate the beamforming result,
$X_A$ may indicate the echo signal to which the time delay value is applied,
U may indicate the basis vectors,
$\alpha$ may indicate the weight with respect to the basis vectors, and
W may indicate the weight applied in the beamforming apparatus 100 which may be defined as a multiplication of U by $\alpha$, i.e., a weighted sum of the basis vectors.

Also, Equation 3 may be defined as Equation 4.

$$Z = X_A^T U^T \alpha = \alpha^T [U X_A] = \alpha^T X_{AU}^T \qquad \text{[Equation 4]}$$

In Equation 4, $X_{AU}$ may indicate the echo signal to which the time delay value is applied and which is projected on each of the basis vectors U.

In more detail, U indicating the basis vectors may be defined as Equation 5.

$$U = [V_1, V_2, \ldots, V_r] \qquad \text{[Equation 5]}$$

In Equation 5, U may indicate a group of the basis vectors,
V may indicate an eigenvector or the basis vector, and
r may indicate the number of the basis vectors to be stored according to the user's determination.

In Equation 5, the basis vector V may function as a fixed window.

Figure 4:
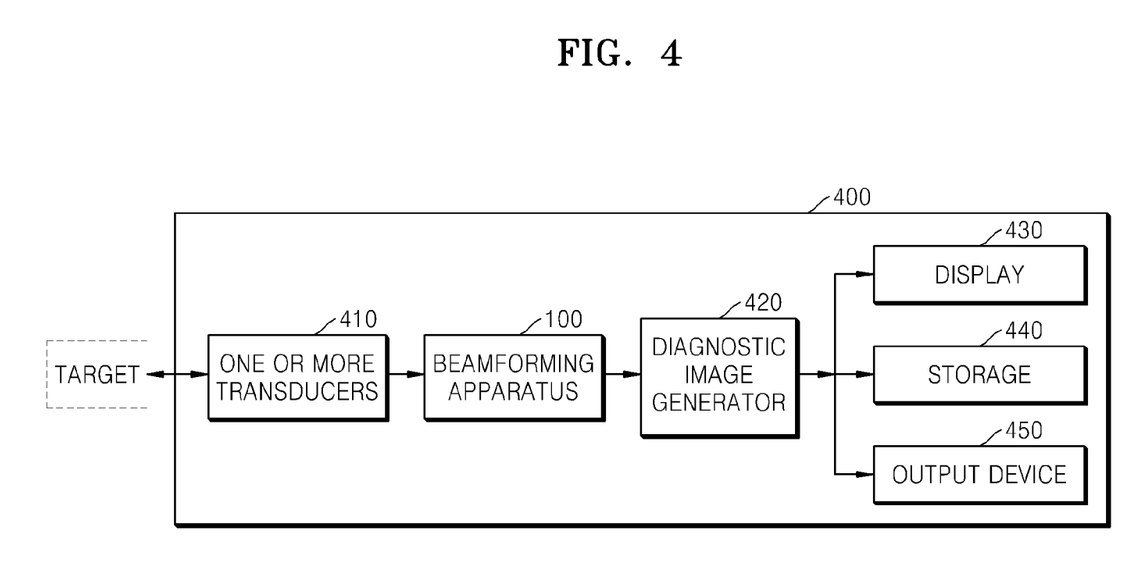
FIG. 4 is a diagram of a medical imaging system, according to an exemplary embodiment.
Figure 5:
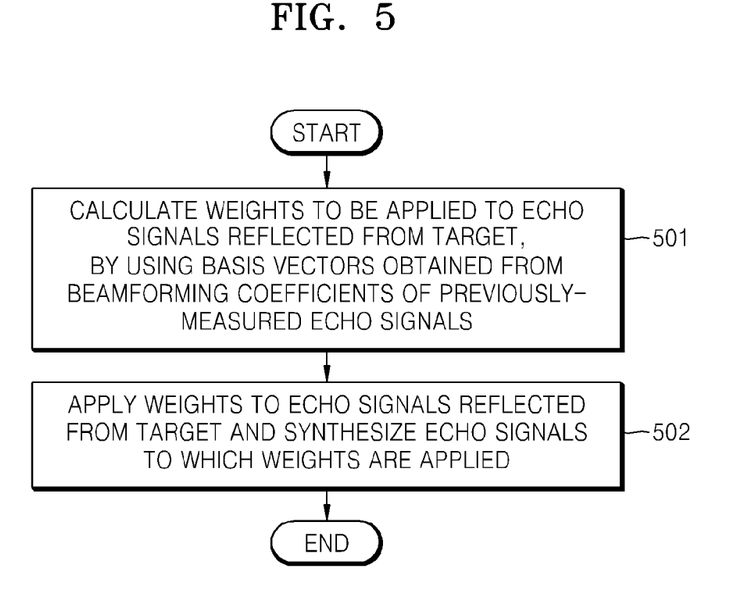
FIG. 5 is a flowchart illustrating a beamforming method, according to an exemplary embodiment.

Referring to FIGS. 4 and 5, the projected echo signal $X_{AU}$ to which the time delay value is applied and which is projected on the basis vectors U may be generated by being projected on the group of the basis vectors U.

As described above, the beamforming apparatus 100 may perform beamforming by multiplying the weight $\alpha$ by the projected echo signal $X_{AU}$ to which the time delay value is applied and which is projected on the basis vectors. In a case where an echo signal of which sub-aperture is 32 is projected on 10 basis vectors, the degree of the echo signal is decreased from 32 to 10, so that the computational amount performed to calculate a weight may be substantially decreased.

For example, the projector 115 projects a steering vector on each of at least some of the basis vectors stored in the storage 110. For example, the number of the at least some of the basis vectors which are projection targets by the projector 115 may be determined by a user. Accordingly, the projector 115 may output a modified steering vector. This will be described in detail with reference to Equations 6 and 8.

As described above, in order to decrease the computational amount with respect to the calculation of the weight, the beamforming apparatus 100 may project the echo signal to which the time delay value is applied to the basis vectors, may project the steering vector to the basis vectors, and may calculate the weight by using the projected echo signal and the projected steering vector.

The weight calculator 120 calculates the weight to be applied to the echo signal reflected from the target object, by using the basis vectors stored in the storage 110. For example, the weight calculator 120 may calculate the weight by using the echo signal projected by the projector 115.

In more detail, the weight calculator 120 may calculate the weight by using Equation 6.

$$\alpha = \frac{R_{\Delta u}^{-1} e_m}{e_m^H R_{\Delta u}^{-1} e_m} \qquad \text{[Equation 6]}$$

In Equation 6, $\alpha$ may indicate the weight,
$R_{\Delta U}$ may be a sample covariance matrix of $X_{\Delta U}$, and
$e_m$ may indicate the modified steering vector.

When the weight calculator 120 calculates an inverse of the sample covariance matrix $R_{\Delta U}$, the weight calculator 120 may perform a diagonal loading technique or an axial smoothing technique to ensure stability.

In Equation 6, $R_{\Delta U}$ may be defined by using Equation 7, and $e_m$ may be defined by using Equation 8.

$$R_{\Delta U} = E[X_{\Delta U} X_{\Delta U}^T] \qquad \text{[Equation 7]}$$

In Equation 7, the sample covariance matrix $R_{\Delta U}$ may be defined as an expectation value with respect to a transpose of the projected echo signal $X_{\Delta U}$ and the projected echo signal $X_{\Delta U}$. For example, the sample covariance matrix $R_{\Delta U}$ in Equation 7 may be obtained by processing $X_{\Delta U}$ in units of sub-arrays and then by reflecting an average value thereto.

$$e_m = Ue \qquad \text{[Equation 8]}$$

In Equation 8, the modified steering vector $e_m$ may be obtained by projecting a steering vector e on the group of the basis vectors U. For example, the steering vector e is used to control a phase of a signal transmitted from the transducer to the target object. Accordingly, when it is assumed that the time delay value for beamforming is already applied to the echo signal with respect to a direction, the steering vector e may correspond to 1.

In this manner, the weight calculator 120 calculates the weight by using the echo signal and the steering vector, which are projected on the basis vectors by the projector 115, so that the computational amount may be substantially decreased.

The synthesizer 130 applies the weight to the echo signal reflected from the target object, by using the basis vectors stored in the storage 110, and synthesizes signals to which the weight is applied, wherein the weight is calculated by the weight calculator 120. For example, the synthesizer 130 applies the weight, which is calculated by the weight calculator 120, to the echo signal projected by the projector 115.

The weight application by the synthesizer 130 may be performed by using Equations 3 and 4, in which the weight $\alpha$ is multiplied by the echo signal $X_{\Delta U}$ to which the time delay value is applied and which is projected on each of the basis vectors, but is not limited thereto.

In this manner, the projector 115 projects the echo signals to the basis vectors, and the synthesizer 130 applies the weight to the projected echo signals, so that the beamforming apparatus 100 may perform a multi-windowing operation on the echo signal reflected from the target.

For example, the synthesizer 130 synthesizes the signals to which the weight is applied. According to a result of the synthesis by the synthesizer 130, as defined via Equations 1 and 2, a reception beam z or Z[n] that is formed in response to the beamforming result may be output.

By doing so, the beamforming apparatus 100 may perform beamforming while the computational amount is substantially decreased.

Hereinafter, the beamforming performed by the beamforming apparatus 100 will now be described in detail with reference to a case in which an echo signal reflected from a target is received by each of M channels. However, an exemplary embodiment is not limited thereto, and, thus, the echo signal reflected from the target may be received by each of M sub-arrays.

For example, an echo signal X reflected from the target object may be defined by using Equation 9.

$$X = [X_1, X_2, \ldots, X_M] \qquad \text{[Equation 9]}$$

In Equation 9, M may indicate a number of channels,
$X_1$ may indicate an echo signal received by a first channel,
$X_2$ may indicate an echo signal received by a second channel, and
$X_M$ may indicate an echo signal received by an $M^{th}$ channel.

The time delay value applicator 105 applies a time delay value Δ to the echo signal X reflected from the target object. For example, an echo signal $X_\Delta$ to which the time delay value is applied by the time delay value applicator 105 may be defined by using Equation 10.

$$X_\Delta = [X_{\Delta 1}, X_{\Delta 2}, \ldots, X_{\Delta M}] \qquad \text{[Equation 10]}$$

In Equation 10, $X_{\Delta 1}$ may indicate an echo signal received by a first channel to which a time delay value Δ1 is applied,
$X_{\Delta 2}$ may indicate an echo signal received by a second channel to which a time delay value Δ2 is applied, and)
$X_{\Delta M}$ may indicate an echo signal received by a $M^{th}$ channel to which a time delay value ΔM is applied.

The storage 110 stores the basis vectors obtained from a beamforming coefficient of a previously-measured echo signal. For example, the basis vectors stored in the storage 110 may indicate a group of the basis vectors, and the group of the basis vectors U may be defined by using Equation 11.

$$U = [V_1, V_2, \ldots, V_r] \qquad \text{[Equation 11]}$$

In Equation 11, r may indicate a number of the stored basis vectors,
$V_1$ may indicate a first basis vector,
$V_2$ may indicate a second basis vector, and
$V_r$ may indicate an $r^{th}$ basis vector.

For example, a number of the stored basis vectors r may be determined by a user and may be an integer equal to or greater than 1 and less than or equal to a number of channels M.

The projector 115 projects the echo signal, which is reflected from the target, on each of at least some of the basis vectors stored in the storage 110.

For example, it is assumed that a user wants to perform beamforming by using k basis vectors from among r basis vectors stored in the storage 110. In this regard, k may be determined by the user and may be an integer equal to or greater than 1. For example, k may be equal to or less than a number of the stored basis vectors r and less than a number of channels M. That is, the number of basis vectors used in the present exemplary embodiment is less than the number of channels.

Accordingly, an echo signal $X_{\Delta U}$ to which a time delay value is applied and which is projected on the k basis vectors by the projector 115 may be defined by Equation 12, wherein the k basis vectors are chosen from among the r basis vectors stored in the storage 110.

$$X_{\Delta U} = [X_{\Delta U1}, X_{\Delta U2}, \ldots, X_{\Delta Uk}] \qquad \text{[Equation 12]}$$

In Equation 12, $X_{\Delta U1}$ may indicate an echo signal projected on the first basis vector $V_1$,
$X_{\Delta U2}$ may indicate an echo signal projected on the second basis vector $V_2$, and)
$X_{\Delta Uk}$ may indicate an echo signal projected on a $k^{th}$ basis vector $V_k$.

Referring to Equations 10 and 12, the delayed echo signal $X_\Delta$ reflected from the target has an M dimension, but the projected echo signal $X_{\Delta U}$ projected by the projector 115 has a k dimension. As described above, k is less than M, so that a dimension of the echo signal may be decreased due to the projection by the projector 115.

For example, the projector 115 projects a steering vector on each of at least some of the r basis vectors stored in the storage 110. A steering vector $e_m$ that is projected on k basis vectors from among the r basis vectors stored in the storage 110, by the projector 115, may be defined by using Equation 13.

$$e_m = [e_{m1}, e_{m2}, \ldots, e_{mk}] \qquad \text{[Equation 13]}$$

In Equation 13, $e_{m1}$ may indicate a steering vector projected on the first basis vector $V_1$,
$e_{m2}$ may indicate a steering vector projected on the second basis vector $V_2$, and
$e_{mk}$ may indicate a steering vector projected on the $k^{th}$ basis vector $V_k$.

The weight calculator 120 calculates a weight by using the echo signal and the steering vector that are projected by the projector 115. For example, the weight calculator 120 may be defined by using Equation 14.

$$\alpha_T = [\alpha_1^T, \alpha_2^T, \ldots, \alpha_k^T] \qquad \text{[Equation 14]}$$

In Equation 14, α1 may indicate a weight to be applied to the echo signal that is projected on the first basis vector $V_1$,
α2 may indicate a weight to be applied to the echo signal that is projected on the second basis vector $V_2$, and
$\alpha_k$ may indicate a weight to be applied to the echo signal that is projected on the $k^{th}$ basis vector $V_k$.

For example, $\alpha_k$ may be calculated by using $X_{\Delta Uk}$ of Equation 12 and $e_{mk}$ of Equation 13.

The synthesizer 130 applies the weight $\alpha^T$ to the echo signals to which the time delay value is applied and which are projected on the basis vectors, respectively, and then synthesizes signals to which weight $\alpha^T$ is applied.

For example, the synthesizer 130 applies the weight $\alpha^T$ to the echo signal $X_{\Delta U}$ to which the time delay value is applied and which is projected on the basis vectors, and a result of the synthesis of the signals to which weight $\alpha^T$ is applied may be defined by using Equation 15.

$$\alpha^T X_{\Delta U} = \alpha_1^T X_{\Delta U1} + \alpha_2^T X_{\Delta U2} + \ldots + \alpha_k^T X_{\Delta Uk} \qquad \text{[Equation 15]}$$

Accordingly, the result of the synthesis by the synthesizer 130 may correspond to the reception beam that is formed according to the beamforming result.

In this manner, the beamforming apparatus 100 may perform beamforming with the decreased computational amount while the resolution of the diagnostic image is not compromised.

FIG. 4 is a diagram of a medical imaging system 400, according to an exemplary embodiment. Referring to FIG. 4, the medical imaging system 400 includes the beamforming apparatus 100, one or more transducers 410, a diagnostic image generator 420, a display 430, a storage 440, and an output device 450.

The beamforming apparatus 100 of FIG. 4 corresponds to an example of the beamforming apparatus 100 shown in FIGS. 1 and 3, thus, exemplary embodiments described above with reference to FIGS. 1 and 3 are applicable to the medical imaging system 400 of FIG. 4, and overlapping descriptions are omitted.

The medical imaging system 400 according to the present exemplary embodiment provides a diagnostic image of a target. For example, the medical imaging system 400 displays the diagnostic image indicating the target, or outputs a signal, which corresponds to the diagnostic image of the target, to an external device that displays the diagnostic image with respect to the target. For example, the diagnostic image may be an ultrasonic image but is not limited thereto.

The one or more transducers 410 exchange a signal with the target. The one or more transducers 410 may be one-dimensional array-transducers but are not limited thereto and, thus, may be two-dimensional array-transducers or three-dimensional array-transducers.

The one or more transducers 410 transmit a transmission signal to the target and receive an echo signal reflected from the target.

The beamforming apparatus 100 calculates a weight to be applied to the echo signal reflected from the target, by using a plurality of basis vectors obtained from a beamforming coefficient of a previously-measured echo signal, applies the calculated weight to the echo signal reflected from the target, and synthesizes signals to which the weight is applied.

For example, the basis vectors obtained from the beamforming coefficient of the previously-measured echo signal may be stored in the beamforming apparatus 100 or the storage 440. Accordingly, the beamforming apparatus 100 may perform beamforming by using at least a number of the stored basis vectors. For example, the number of the basis vectors may be determined by a user.

As described above, the beamforming apparatus 100 calculates the weight by using the basis vectors, and applies the weight to the echo signal, so that the beamforming apparatus 100 may perform beamforming with the decreased computational amount.

For example, the one or more transducers 410 and the beamforming apparatus 100 may be included in a probe, but this is not limiting. Thus, the beamforming apparatus 100 may be included in a main body of the medical imaging system 400, and the one or more transducers 410 may be included in the probe.

The diagnostic image generator 420 generates the diagnostic image by using signals output from the beamforming apparatus 100. The diagnostic image generator 420 may include a digital signal processor (DSP) (not shown) and a digital scan converter (DSC) (not shown). The DSP performs a signal processing operation on the signals output from the beamforming apparatus 100. The DSC performs scan conversion on image data formed by using the signals on which the signal processing operation is performed, and thus generates the diagnostic image.

The display 430 displays the diagnostic image generated by the diagnostic image generator 420. For example, the display 430 may include output devices including a display panel, a mouse, a liquid crystal display (LCD) screen, a monitor, and the like that are arranged in the medical imaging system 400.

However, the medical imaging system 400 may lack some of the above devices, for example, the display 430. For example, the output device 450 may output the diagnostic image generated by the diagnostic image generator 420 to an external display device (not shown).

The storage 440 stores the diagnostic image generated by the diagnostic image generator 420, and data generated during operations of the medical imaging system 400. The storage 440 may include a hard disk drive (HDD), a read-only memory (ROM), a random access memory (RAM), a flash memory, and/or a memory card.

The output device 450 may exchange data with an external device via a wired or wireless network or wired serial communication. For example, a network includes Internet, a local area network (LAN), a wireless LAN, a wide area network (WAN), a personal area network (PAN), or the like, but this is not limited thereto. Thus, the network may include a different type of a network capable of transmitting and receiving information, and the external device may include another medical imaging system which is located in a remote location, a general-use computer system, a facsimile, or the like.

The storage 440 and the output device 450 may further include image reading and searching functions and may be formed as one integrated device such as a Picture Archiving Communication System (PACS).

As described above, the beamforming apparatus 100 does not demand the great computational amount in performing beamforming. Thus, the medical imaging system 400 may generate a high-resolution diagnostic image in real-time.

FIG. 5 is a flowchart illustrating a beamforming method, according to an exemplary embodiment. Referring to FIG. 5, the beamforming method includes operations that are processed in chronological order by the beamforming apparatus 100 or the medical imaging system 400 illustrated in FIGS. 1, 3, and 4. Thus, although the features described above regarding the beamforming apparatus 100 or the medical imaging system 400 illustrated in FIGS. 1, 3, and 4 are omitted hereinafter, the features may be applied to the beamforming method of FIG. 5.

In operation 501, the weight calculator 120 calculates weights to be applied to echo signals reflected from a target, by using a plurality of basis vectors obtained from beamforming coefficients of previously-measured echo signals.

In operation 502, the synthesizer 130 applies the weights calculated in operation 501 to the echo signals reflected from the target, and synthesizes the echo signals to which the weights are applied.

As described above, according to one or more exemplary embodiments, the beamforming method may perform the beamforming to obtain a high-resolution diagnostic image in real-time.

Also, according to one or more exemplary embodiments, the computational amount in performing the beamforming for obtaining the high-resolution diagnostic image in real-time may be substantially decreased.

Exemplary embodiments can be written as computer programs and can be implemented in general-use computers that execute the programs using a computer-readable recording medium. A data structure used in exemplary embodiments can be written in a computer-readable recording medium through various means. Examples of the computer-readable recording medium include magnetic storage media (e.g., ROM, floppy disks, hard disks, etc.), optical recording media (e.g., CD-ROMs, or DVDs), etc.

It should be understood that exemplary embodiments described therein should be considered in a descriptive sense only and not for purposes of limitation. Descriptions of features or aspects within each exemplary embodiment should be considered as available for other similar features or aspects in other exemplary embodiments.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound apparatus configured to acquire ultrasound signals as echo signals reflected from a target, the ultrasound apparatus comprising: a transducer which acquires the echo signals reflected from the target;
a storage which stores basis vectors obtained from beamforming coefficients of previously-measured echo signals;
a projector configured to project the acquired echo signals on a k number of the basis vectors;
a weight calculator which calculates weights to be applied to the echo signals reflected from the target, by using the projected echo signals; and
a synthesizer which applies the weights to corresponding echo signals reflected from the target, and synthesizes the echo signals to which the weights are applied,
wherein the k number is equal to or greater than 1 and less than a number of reception channels which receive the echo signals reflected from the target.

2. The ultrasound apparatus of claim 1, wherein the synthesizer applies the weights to the projected echo signals, and synthesizes the projected echo signals to which the weights are applied.

3. The ultrasound apparatus of claim 1, wherein the projector projects a steering vector on at least one of the basis vectors,
the weight calculator calculates the weights by using the projected echo signals and the projected steering vector, and
the synthesizer applies the weights to the projected echo signals, and synthesizes the echo signals to which the weights are applied.

4. The ultrasound apparatus of claim 1, wherein the k number is determined by a user.

5. The ultrasound apparatus of claim 1, wherein the storage stores the basis vectors obtained by performing a principal component analysis (PCA) on the beamforming coefficients of the previously-measured echo signals.

6. The ultrasound apparatus of claim 1, wherein the synthesizer applies a weighted sum to the echo signals reflected from the target, and synthesizes the echo signals to which the weighted sum is applied, and
the weighted sum is determined with respect to at least some of the basis vectors.

7. A medical imaging system comprising:
a transducer which acquires the echo signals reflected from a target; a beamforming apparatus which projects echo signals reflected from a target on a k number of basis vectors obtained from beamforming coefficients of previously-measured echo signals, calculates weights to be applied to the echo signals reflected from the target, by using the projected echo signals, applies the weights to the acquired echo signals, and synthesizes the echo signals to which the weights are applied; and
a diagnostic image generator which generates a diagnostic image by using signals output from the beamforming apparatus,
wherein the k number is equal to or greater than 1 and less than a number of reception channels which receive the echo signals reflected from the target.

8. The medical imaging system of claim 7, further comprising a storage which stores the basis vectors.

9. The medical imaging system of claim 7, wherein the k number is determined by a user.

10. The medical imaging system of claim 7, wherein the beamforming apparatus applies the weights to the projected echo signals.

11. A beamforming method of an ultrasound apparatus configured to acquire ultrasound signals as echo signals reflected from a target, the beamforming method comprising:
acquiring the echo signals reflected from the target; projecting the acquired echo signals on a k number of basis vectors obtained from beamforming coefficients of previously-measured echo signals;
calculating weights to be applied to the echo signals reflected from the target, by using the projected echo signals;
applying the weights to the echo signals reflected from the target; and
synthesizing the echo signals to which the weights are applied,
wherein the k number is equal to or greater than 1 and less than a number of reception channels which receive the echo signals reflected from the target.

12. The beamforming method of claim 11, wherein the synthesizing comprises applying the weights to the projected echo signals, and synthesizing the echo signals to which the weights are applied.

13. The beamforming method of claim 12, further comprising projecting a steering vector on at least one of the basis vectors,
wherein the calculating the weights comprises calculating the weights by using the projected echo signals and the projected steering vector.

14. The beamforming method of claim 11, wherein the k number is determined by a user.

15. The beamforming method of claim 11, wherein the basis vectors are obtained by performing a principal component analysis (PCA) on the beamforming coefficients of the previously-measured echo signals.

16. The beamforming method of claim 11, wherein the synthesizing comprises applying a weighted sum to the echo signals reflected from the target and synthesizing the echo signals to which the weighted sum is applied,
wherein the weighted sum is determined with respect to at least some of the basis vectors.

17. A non-transitory computer-readable recording medium having recorded thereon a program which, when executed by a computer, causes the computer to execute the beamforming method of claim 11.

18. A method of an ultrasound apparatus configured to acquire ultrasound signals as echo signals reflected from a target, the method comprising:
acquiring the echo signals reflected from the target; obtaining basis vectors from beamforming coefficients of previously-measured echo signals;
storing, in a storage, an r number of the obtained basis vectors, the r number being greater than or equal to 1;
determining a k number of the basis vectors, the k number being smaller than the r number of the basis vectors stored in the storage and smaller than an M number of reception channels;
projecting the acquired echo signals reflected from the target on the k basis vectors;
calculating weights based on the echo signals projected on the k basis vectors;
applying the weights to the projected echo signals; and synthesizing the weighted echo signals.

19. The method of claim 18, wherein the calculating comprises:
projecting a steering vector on the k basis vectors; and calculating the weights by using the projected echo signals and the steering vector, which have been projected on the k basis vectors.

20. The ultrasound apparatus of claim 1, wherein the previously-measured echo signals are obtained by being reflected from a same target as currently reflected echo signals to which the weights are being applied.

* * * * *